United States Patent [19]

Higa et al.

[11] Patent Number: 4,921,873

[45] Date of Patent: May 1, 1990

[54] ANTIVIRAL AND ANTITUMOR CYCLOHEXADIENONE COMPOSITIONS

[75] Inventors: Tatsuo Higa, Okinawa; Kenneth M. Snader, Vero Beach, Fla.

[73] Assignee: Harbor Branch Oceanographic Institution, Inc., Ft. Pierce, Fla.

[21] Appl. No.: 744,620

[22] Filed: Jun. 14, 1985

Related U.S. Application Data

[63] Continuation-in-part of Ser. No. 682,278, Dec. 17, 1984, abandoned.

[51] Int. Cl.$^5$ .................... A61K 31/12; A61K 35/80; C07C 49/597
[52] U.S. Cl. .................... 514/546; 424/195.1; 514/548; 514/550; 514/690; 560/231; 560/248; 568/366; 568/377
[58] Field of Search ............ 560/231, 248, 227, 228; 568/366, 377; 514/546, 548, 550, 690; 424/195.1, 104

[56] References Cited

U.S. PATENT DOCUMENTS

| | | | |
|---|---|---|---|
| 4,162,308 | 7/1979 | Calvin et al. | 514/546 |
| 4,162,309 | 2/1979 | Calvin et al. | 514/546 |
| 4,708,962 | 11/1987 | Higa et al. | 514/475 |

*Primary Examiner*—Werren B. Lone
*Attorney, Agent, or Firm*—Carroll F. Palmer

[57] ABSTRACT

This invention relates to antiviral and antitumor compositions, a process for producing the compositions and a method for inhibiting viruses and tumors utilizing the compositions. More particularly, the compositions are cyclohexadienone derivatives which are derived from red alga *Desmia hornemanni*.

20 Claims, No Drawings

ANTIVIRAL AND ANTITUMOR CYCLOHEXADIENONE COMPOSITIONS

CONTINUING APPLICATION DATA

This is a continuation-in-part of U.S. patent application Ser. No. 682,278 filed December 17, 1984, now abandoned.

FIELD OF THE INVENTION

This invention relates to new cyclohexadienone derivatives which have useful antiviral and antitumor activity. More particularly, this invention relates to cyclohexadienone derivatives with antiviral and antitumor activities which are derived from marine organisms, i.e. red alga.

BACKGROUND OF THE INVENTION

Viral diseases inflict man, plants, insects, and animals. The prevention and control of viral diseases have important health and economic implications.

Viral diseases contribute to inflictions in humans including common colds, herpes and cancer and the importance of their control is obvious. Also important is control of viral diseases in animals for economic reasons as well as the ability of such animals to become virus reservoirs or carriers which facilitate the spreading of viral diseases to humans. Viral plant diseases have been known to have a disruptive effect on the cultivation of fruit trees, tobacco, and various vegetables. Insect viral diseases are also of interest because of the insects' ability to transfer viral diseases to humans.

The prevention and control of viral diseases is thus of prime importance to man and considerable research has been devoted to antiviral measures. Certain methods and chemical compositions have been developed which aid in inhibiting, controlling or destroying viruses but new methods and antiviral chemical compositions are needed.

U.S. Pat. Nos. 4,162,308 and 4,162,309 to Calvin and Ellis describe that water soluble extracts from marine red algae have been found to be effective to inhibit the growth of certain herpes viruses.

U.S. Pat. No. 4,162,308 describes water soluble extracts from marine red algae selected from a group consisting of *Turnerella mertensiana, Schizymenia epiphytica, Turnerella pennyi* and mixtures thereof as effective to inhibit the growth of herpes simplex virus, type 1 and type 2, and herpes zoster, and to relieve the pain caused by infection attributable to such viruses.

U.S. Pat. No. 4,162,309 describes the use of water soluble extracts from marine red algae selected from a group consisting of *Neodilsea americana* and *Neodilsea integra* and mixtures thereof to inhibit the growth of herpes simplex virus, type 1 and type 2, and herpes zoster, and to relieve the pain caused by infection attributable to such viruses. The entire disclosures of U.S. Pat. Nos. 4,162,308 and 4,162,309 are hereby incorporated herein by reference.

Crews et al in "Bio-Active Monoterpenes from Red Seaweeds", *Phytochemistry* Vol. 23 No. 7 Pp. 1449–1451, Pergamon Press Ltd., Great Britain, 1984, describe the bioactivity of seaweed derived monoterpenes. Crews et al disclose halogenated monoterpenes which are extracted from red algae *Chondrococcus hornemanni* with methylene chloride. The halogenated monoterpenes were shown to be bioactive in various applications and biotoxic against insects.

In addition to the water soluble red algae extractions described in the above noted U.S. Patent applications to Calvin and Ellis and the halogenated monoterpenes of Crews et al other compounds have been isolated from red algae and marine organisms known as sea hares which are mollusks which diet on red algae. These compounds include halogenated chamigrenes and have been described in various literature references including P. J. Scheuer, Ed. *Marine Natural Products* Volume 1 (Martin) and Volume 5 (Erickson) Academic Press, 1978; 1983, the entire disclosure of this reference is hereby incorporated herein by reference.

Prevention, control of the growth and regression of tumors in mammals is also of importance to man. Considerable research has been devoted to oncology and antitumor measures. While certain methods and chemical compositions have been developed which aid in inhibiting or controlling tumors new methods and antitumor chemical compositions are need.

It has now been found that certain cyclohexadienone compounds derived from extracts of red algae possess useful antiviral and antitumor activity.

SUMMARY OF THE INVENTION

It is therefore an object of the invention to provide novel compositions which are useful as antiviral and antitumor agents and a process for producing such novel antiviral and antitumor compositions.

It is an additional object of the invention to provide a method for inhibiting viruses and tumors utilizing novel antiviral and antitumor compositions, respectively.

Additional objects and advantages of the invention will be set forth, in part, in the description which follows and in part will be obvious from this description, or may be learned by the practice of the invention. The objects and advantages of the invention are realized and obtained by means of the compositions, processes, methods, and the combinations particularly pointed out in the appended claims.

To achieve the objects in accordance with the purposes of the invention, as embodied and fully described here, the invention comprises a composition of the general formula (I):

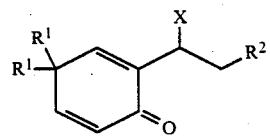

wherein both $R_1$ groups are the same or different and are hydrogen or a lower alkyl group, X is a lower alkyl, hydroxy, lower acyloxy, lower alkoxy, fluoro, chloro, bromo or iodo group, and $R_2$ is hydroxy, a lower acyloxy group, a halogenated lower acyloxy group or halogen.

In preferred embodiments of the invention, $R_1$ is a methyl group, $R_2$ is an acetyloxy group, and X is methyl, chloro, or bromo.

In a more preferred embodiment of the invention, the invention comprises a composition of the formula:

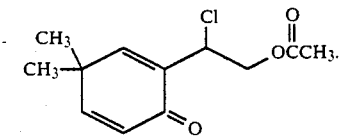

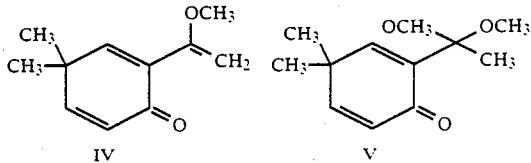

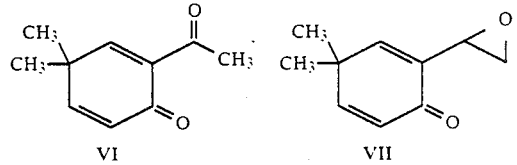

As embodied and fully described herein, the invention also comprises an antiviral or antitumor composition comprising, as active ingredient, an effective antiviral or antitumor amount of one or more of the compositions according to Formula I or preferably Formula II and a non-toxic pharmaceutically acceptable carrier or diluent.

As embodied and broadly described herein, the invention also comprises a process to produce the compounds of Formula I comprising the steps of: collecting red alga; contacting the alga with a suitable organic solvent to obtain an extract; and isolating a compound of Formula I. Preferably, the process comprises the steps of: collecting red alga, particularly Desmia hornemanni; contacting the alga with a suitable organic first solvent to obtain extract; removing the solvent containing a derivative of the first compound of Formula I, preferably an alcohol derivative of Formula II; isolating the derivative of Formula II by conventional means, preferably chromatography; and acetylating the alcohol derivative to yield the compound of Formula II.

As embodied and fully described herein, the invention further comprises a method for inhibiting viruses or tumors comprising contacting a virus or tumor with an effective antiviral or antitumor amount of one or more compositions of Formula I or preferably Formula II.

In accordance with the purposes of the invention, as embodied and fully described herein, the invention further comprises a composition of the general formula (III):

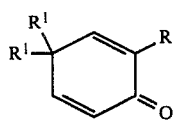

wherein R is:

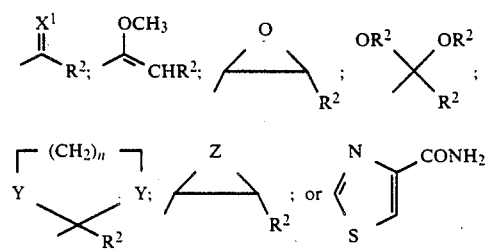

wherein $X^1$ is an oxygen, sulfur or an imine group; Y is oxygen or sulfur; Z is oxygen, sulfur or an imine group; wherein both $R^1$ groups are the same and are hydrogen or a lower alkyl group, $R^2$ is H or a lower alkyl group; and n is from 1 to 5.

In preferred embodiments of the invention, $R^1$ and $R^2$ are methyl groups, and $X^1$ and Y are oxygen.

In a more preferred embodiment of the invention, the invention comprises compositions of the Formulae:

As embodied and fully described herein, the invention also comprises an antitumor composition comprising, as active ingredient, an effective antitumor amount of one or more of the compositions according to Formula I or III or preferably one of Formula IV, V, VI or VII and a non-toxic pharmaceutically acceptable carrier or diluent.

As embodied and broadly described herein, the invention also comprises a process to produce the compounds of Formula III comprising the steps of: collecting red alga; contacting the alga with a suitable organic solvent to obtain an extract; and synthesizing and isolating a compound of Formula III.

As embodied and fully described herein, the invention further comprises a method for inhibiting tumors comprising contacting a tumor with an effective antitumor amount of one or more compositions of Formula I or III or preferably one of Formula IV, V, VI or VII.

It is to be understood that both the foregoing general and the following detailed description are exemplary and explanatory only and are not intended to be restrictive of the invention as claimed.

DETAILED DESCRIPTION OF THE PREFERRED EMBODIMENTS OF THE INVENTION

Reference will now be made in detail to present preferred embodiments of the invention, examples of which are illustrated in the following example section.

In accordance with the invention, a composition is provided of the formula:

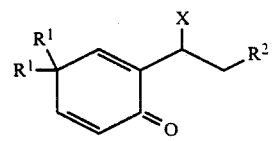

wherein both $R_1$ groups are the same or different and are hydrogen or a lower alkyl group, X is a lower alkyl, hydroxy, lower acyloxy, lower alkoxy, fluoro, chloro, bromo or iodo group, and $R_2$ is hydroxy, a lower acyloxy group, a halogenated lower acyloxy group or a halogen.

Preferably, the lower alkyl and acyloxy groups have from one to five carbon atoms, more preferably from one to three carbon atoms, and most preferably, the lower alkyl group is methyl and the lower acyloxy group is acetyloxy.

Preferably, X is a methyl, chloro or bromo group, more preferably, X is a chloro group.

More particularly, a preferred embodiment of the invention comprises a composition of the structure II as indicated below:

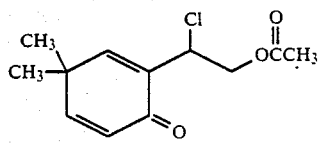

II

In accordance with the invention an antiviral composition is provided comprising as active ingredient an effective antiviral amount of one or more of the compositions described above and identified by Formulas I and II and a non-toxic pharmaceutically acceptable carrier or diluent. While effective amounts may vary, as conditions in which the antiviral compositions are used vary, a minimal dosage required for activity is generally between 50 and 200 micrograms against 25–80 plaque-forming units of virus. Useful examples of non-toxic pharmaceutically acceptable carriers or diluents include, but are not limited to, the following: ethanol; dimethyl sulfoxide; and glycerol.

In accordance with the invention, a process to produce a compound according to Formula I comprises the steps of: collecting red alga, particularly *Desmia hornemanni* (also known as *Chondrococcus hornemanni*); contacting the alga with a suitable organic solvent to obtain an extract of the solvent; and isolating a compound according to Formula I.

A detailed description and explanation of a preferred embodiment of the process of the invention to produce the compound according to Formula I is as follows. Red alga, *Desmia hornemanni* is collected at Cape Zampa, Okinawa. The alga is then contacted with acetone (a first solvent) to obtain an acetone extract from the red alga. The acetone extract is then concentrated by evaporation through either heat or reduced pressure and the acetone residue is contacted with methylene chloride to obtain a methylene chloride extract.

While acetone and methylene chloride are the presently preferred choices for first and second solvents, other suitable solvents may be substituted for acetone and/or methylene chloride. A suitable first solvent should be capable of extracting a compound according to Formula I from other components of the red alga. Suitable first solvents which may be substituted for acetone include, but are not limited to, the following organic solvents: methyl ethyl ketone; ethyl acetate; methanol; ethanol; and methyl isobutyl ketone. A suitable second solvent should be capable of extracting and separating the compound of Formula I from other components that may be present in the first solvent extract. Suitable second solvents which may be substituted for methylene chloride include, but are not limited to, the following organic solvents: chloroform; trichloroethylene; hexane; and lower alkanes. Different ratios of first to second solvents may be used in the invention as would be known to those skilled in the art.

The methylene chloride extract is removed and concentrated by evaporation of the methylene chloride solvent by either gentle heating or reduced pressure. An alcohol derivative of the compound of Formula II is isolated from the methylene chloride extract by chromatography.

Any suitable chromatography technique may be used, but it has been found that first subjecting the methylene chloride extract to chromatography on a silica gel column, by eluting with hexane-acetone in an approximate ml. ratio of 7:3 hexane to acetone to obtain a major fraction of the alcohol derivative of Formula II and then further separating the major fraction on a thin layer chromatography grade silica gel column by flash chromatography yields the pure alcohol derivative of the compound according to Formula II. Other eluents and columns may be substituted as would be known to those skilled in the art.

The alcohol derivative of the compound of Formula II was found to decompose at room temperature in two hours so it is important to carry out the next step as soon as possible.

The alcohol derivative of the compound of Formula II is acetylated with acetic anhydride and pyridine mixture in a ml. ratio of approximately 1:1 of acetic anhydride to pyridine for about ten minutes. While a mixture of acetic anhydride and pyridine is the present preferred choice of acetylation agents other suitable agents may be substituted such as, for example: isopropenyl acetate and acetyl chloride substituted for acetic anhydride; and N-methyl morpholine and N-methyl pyrrolidine substituted for pyridine. The excess acetic anhydride and pyridine is removed by evaporation to yield pure compound according to Formula II.

In accordance with the present invention, virus cells are inhibited in growth or killed by a method comprising contacting a virus with an effective antiviral amount of one or more compositions according to Formulas I and/or II. The minimal effective amount as stated above is generally from 50 to 100 micrograms for 25 to 80 plaque forming units of virus cells. The compound of Formulas I and II are active for inhibiting or killing a diverse range of viruses including, but not limited to, the RNA viruses, vesicular stomatitis (herein "VSV"), arenaviruses, coronaviruses, influenza viruses and the DNA viruses, herpes simplex-I (herein "HSV-I"), other herpes viruses, adenoviruses and papovaviruses.

The effectiveness of the compositions of the invention for inhibiting virus cells indicates that the compositions of Formulae I and II should also be useful in controlling viral infections in host animals and plants which are caused by a virus which is thus inhibited or destroyed. Viral infections which may be controlled by utilizing compositions of the present invention include, but are not limited to, those caused by RNA viruses such as arenaviruses, coronaviruses, reoviruses, influenza viruses, and viral infections caused by the DNA viruses such as herpes viruses, adenoviruses and papova viruses. The invention may also be useful in controlling common viral infections of plants.

In accordance with the invention, a composition is provided of the formula:

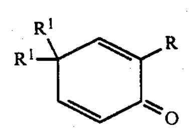

III wherein R is:

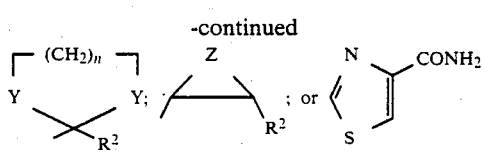

wherein $X^1$ is an oxygen, sulfur or an imine group; Y is oxygen or sulfur; Z is oxygen, sulfur or an imine group; wherein both $R^1$ groups are the same or different and are hydrogen or a lower alkyl group, $R^2$ is H or a lower alkyl group; and n is from 1 to 5.

Preferably, the lower alkyl groups have from one to five carbon atoms, more preferably from one to three carbon atoms, and most preferably, the lower alkyl group is methyl.

Preferably, $X^1$ and Y are oxygen.

More particularly, a preferred embodiment of the invention comprises a composition of the structure IV, V, VI or VII as indicated below:

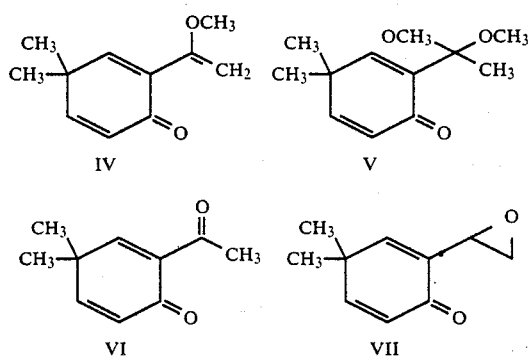

In accordance with the invention an antitumor composition is provided comprising as active ingredient an effective antitumor amount of one or more of the compositions described above and identified by Formulas I-VII and a non-toxic pharmaceutically acceptable carrier or diluent. While effective amounts may vary, as conditions in which the antitumor compositions are used vary, a minimal dosage required for activity is generally between 1 and 100 micrograms against $10^5$ tumor cells. Useful examples of non-toxic pharmaceutically acceptable carriers or diluents include, but are not limited to, the following: ethanol; dimethyl sulfoxide; and glycerol.

In accordance with the invention, a process to produce a compound according to Formula III comprises the step of: collecting red alga, particularly *Desmia hornemanni* (also known as *Chondrococcus hornemanni*); contacting the alga with a suitable organic solvent to obtain an extract of the solvent; and synthesizing and isolating a compound according to Formula III.

A detailed description and explanation of a preferred embodiment of the process of the invention for producing a compound according to Formula III is as follows. Red alga, *Desmia hornemanni* is collected at Cape Zampa, Okinawa. The alga is then contacted with acetone (a first solvent) to obtain an acetone extract from the red alga. The acetone extract is then concentrated by evaporation through either heat or reduced pressure and the acetone residue contacted with methylene chloride to obtain a methylene chloride extract.

While acetone and methylene chloride are the presently preferred choices for first and second solvents, other suitable solvents may be substituted for acetone and/or methylene chloride. A suitable first solvent should be capable of extracting a compound according to Formula I from other components of the red alga. Suitable first solvents which may be substituted for acetone include, but are not limited to, the following polar organic solvents: methyl ethyl ketone; ethyl acetate; methanol; ethanol; and methyl isobutyl ketone. A suitable second solvent should be capable of extracting and separating the compound of Formula I from other components that may be present in the first solvent extract. Suitable second solvents which may be substituted for methylene chloride include, but are not limited to, the following organic solvents: chloroform; trichloroethylene; hexane; and lower alkanes. Different ratios of first to second solvents may be used in the invention as would be known to those skilled in the art.

The methylene chloride extract is removed and concentrated by evaporation of the methylene chloride solvent by either gentle heating or reduced pressure. An alcohol derivative (VIII) of a compound according Formula I is isolated from the methylene chloride extract by chromatography. The alcohol derivative has the following Formula:

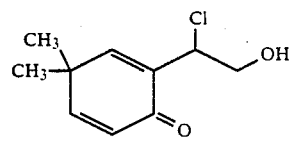

Any suitable chromatography technique may be used, but it has been found that first subjecting the methylene chloride extract to chromatography on a silica gel column, by eluting with hexane-acetone in an approximate ml. ratio of 7:3 hexane to acetone to obtain a major fraction containing a compound of Formula VIII and then further separating the major fraction on a thin layer chromatography grade silica gel column by flash chromatography yields pure Formula VIII. Other eluents and columns may be substituted as would be known to those skilled in the art. The compound of Formula VIII was found to decompose at room temperature in two hours so it is important to carry out the next synthesis steps as soon as possible.

To prepare the preferred embodiments of the invention according to Formula IV, V, VI and VII the following synthesis steps are taken to prepare these compounds from the compound of Formula VIII.

Compounds according to formula IV and V are synthesized from a halogen derivative of the compound of Formula I having the Formula:

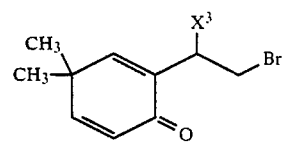

wherein $X^3$ is Cl or Br.

A compound of Formula IX is obtained by isolating a volatile oil fraction from the methylene chloride extract subjected to chromatography as described above for obtaining the alcohol derivative of Formula I (Formula VIII), and obtaining from said volatile oil fraction a halogen derivative of the compound of Formula I having the Formula IX.

The halogen derivative IX is treated with a base such as potassium hydroxide in methanol (e.g. 10% KOH-methanol) to yield (after isolation, e.g., separation by thin layer chromatography) a major amount of a ketal of formula V and a minor amount of a vinyl ether of Formula IV.

A compound according to Formula VI is obtained by hydrolysis of the ketal of Formula V with, for example, methanol and hydrochloric acid (e.g. 1:1 by volume of MeOH: 5N HCl).

A compound according to Formula VII is synthesized by treating a compound of Formula VIII, obtained as described above, with a base such as potassium hydroxide and dioxane (e.g. 1:1 by volume of 1% KOH in $H_2O$: dioxane).

In accordance with the present invention, tumors and tumor cells are inhibited by a method comprising contacting a tumor with an effective antitumor amount of one or more compositions according to Formulae I–VII. The minimal effective amount as stated above is generally from 1 to 100 micrograms for $10^5$ tumor cells. The compound of Formulae I–VII are active for inhibiting a diverse range of tumors including, but not limited to human lung, colon and mammary tumors such as lung carcinoma A549, ileocecal adenocarcinoma HCT-8, and human breast carcinoma MCF-7.

The effectiveness of the compositions of the invention for inhibiting tumors indicates that the compositions of Formula I–VII should also be useful in controlling tumors in host animals.

It is therefore apparent that the compositions of the invention, the processes for producing the compositions of the invention and the methods for utilizing the compositions of the invention to inhibit viruses and tumors are effective for inhibiting or destroying viruses and tumors and therefore controlling diseases caused by or related to such viruses and tumors in fulfillment of the objects of the invention.

EXAMPLES

The invention will now be illustrated by examples. The examples are not intended to be limiting of the scope of the present invention. In conjunction with the detailed and general description above, the examples provide further understanding of the present invention and outline a process for producing compositions of the invention.

The following examples represent preferred embodiments of the compositions, processes and methods of the invention for satisfying the stated objects of the invention. The starting materials and reagents in the examples whose method of preparation are not indicated, are commercially available from sources known to the art such as chemical supply houses.

Example 1

Preparation of:

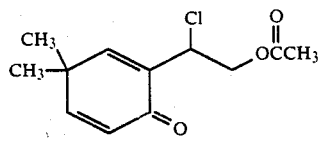

2000 grams of red alga *Desmia hornemanni* were collected and placed in a 5000 ml. vessel and 2000 mls. of acetone was added to the vessel and the mixture was vigorously agitated to produce a slurry.

The slurry was filtered to provide an acetone extract. The acetone extract was concentrated under vacuum at room temperature and admixed with 100 mls. of methylene chloride in a separatory funnel. The methylene chloride fraction was removed and concentrated to give 13.2 gms of crude oil.

The methylene chloride extract was subjected to chromatography on a silica gel column, by eluting with 7:3 hexane-acetone. A major fraction containing the alcohol derivative of Formula II illustrated below as Formula VIII:

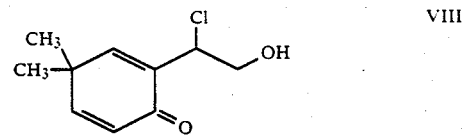

was further separated on a thin layer chromatography grade silica gel column by flash chromatography to obtain the pure compound of Formula VIII, $[\alpha]_D^{21}$ $-87.2°$ (C 1.29, $CH_2CH_2$). The compound of Formula VIII was immediately subjected to acetylation by admixing 100 milligrams of the compound of Formula VIII with 0.1 ml. of acetic anhydride and 0.1 ml. of pyridine. Excess acetic anhydride and pyridine was removed by evaporation with gentle heating and under reduced pressure to give an oil which was further purified by chromatography on silca gel using an eluting solvent of 1:1 of hexane:ethylacetate to give a pure yellow oil of Formula II $[\alpha]_D^{21}$ $-56.8$ (C 0.84, $CHCl_2$). The absolute configuration of the compound is not yet known.

Example 2

Preparation of IV and V

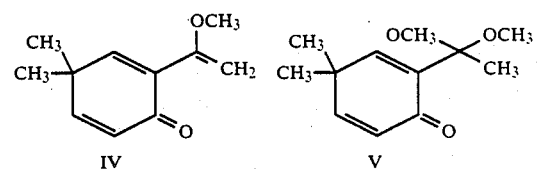

2000 grams of red alga *Desmia hornemanni* were collected and placed in a 5000 ml. vessel and 2000 mls. of acetone was added to the vessel and the mixture was vigorously agitated to produce a slurry.

The slurry was filtered to provide an acetone extract. The acetone extract was concentrated under vacuum at room temperature and admixed with 100 mls. of methylene chloride in a separatory funnel. The methylene chloride fraction was removed and concentrated to yield 13.2 gms. of crude oil.

The methylene chloride extract was subjected to chromatography on a silica gel column, by eluting with 7:3 hexane-acetone. A volatile oil fraction was obtained which contained a halogen derivative of Formula I illustrated below as Formula IX (wherein $X^3$ is Cl or Br):

11

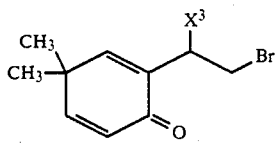

A sample of IX (47.2 mg) was treated with 10% KOH-MeOH at room temperature for 30 minutes giving a reaction mixture with two major spots on a tlc plate (CHCl$_3$). The mixture was separated by a preparative tlc with chloroform to give ketal (V) (Rf=0.3, 18.3 mg 53.4%), and vinyl ether (IV) (Rf=0.5, 8.3 mg, 28.6%).

Ketal (V) has the following characteristics: oil, λmax (EtOH) 235 nm (ε 7900); IR (film) 2960, 2830, 1660, 1635, 1470, 1370, 1270, 1190, 1175, 1150, 1110, 1055, 870 cm$^{-1}$; $^1$H NMR (CCl$_4$) δ7.03 (1H, d, J=3.2 H$_Z$), 6.65 (1H, dd, J=10.0, 3.2 H$_Z$), 6.00 (1H, d, J=10.0 H$_Z$), 3.06 (6H, s), 1.50 (3H,s), 1.30 (6H,s).

Vinyl ether (IV) had the following characteristics: oil, λmax (EtOH) 235 (ε 6000), 218 nm (ε 14000); IR (film) 2960, 1665, 1625, 1580, 1400, 1285, 1080, 840 cm$^{-1}$; $^1$H NMR (CCl$_4$)δ6.97 (1H, d J=3.2 H$_Z$), 6.53 (1H, dd, J=10.0 H$_Z$), 6.00 (1H, d, J=10 H$_Z$), 5.31 (1H, d, J=2.0 H$_Z$), 4.25 (1H, d, J=2.0 H$_Z$), 3.53 (3H, s), 1.30 (6H, s).

Example 3

Alternatively, the ketal (V) can be produced by treating a sample (9.3 mg) of IX in 5N methanolic KOH (1 ml) allowing it to stand at room temperature for 20 hours. After adding 5.0 ml. water the mixture was extracted with CH$_2$Cl$_2$. The CH$_2$Cl$_2$ solution was dried over sodium sulfate and concentrated to give ketal (V) (6.4 mg, 87-97%).

Example 4

Preparation of VI:

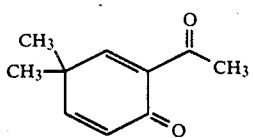

Ketal (V) (6.9 mg) produced according to the procedures of either Examples 2 or 3 was dissolved in 0.1 ml of MeOH and 0.1 ml of 5N HCl. After standing for 10 min the solution was extracted with CHCl$_3$ to give 4.5 mg (79.4%) of (VI) as an oil with the following characteristics: λmax (EtOH) 205 (ε 7500), 234 nm (ε 9200); IR (film) 2980, 2940, 2875, 1695, 1665, 1630, 1600, 1400, 1360, 1260, 935, 840 cm$^{-1}$; $^1$H NMR (CDCL$_3$)δ7.50 (1H, d, J=3.0 H$_Z$), 6.77 (1H, dd, J=10.0, 3.0 H$_Z$), 6.12 (1H, d, J=10.0 H$_Z$), 2.50 (3H, s), 1.33 (6H, s).

Example 5

Preparation of VII:

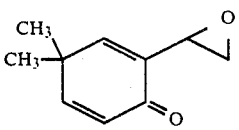

A mixture of (VIII) (157.8 mg), 2 ml of 1% KOH/H$_2$O, and 2 ml of dioxane was heated under reflux for two hours. After removing dioxane in vacuo the reaction mixture was extracted with chloroform. The extract was separated on a silica gel column with chloroform to give 62 mg of starting material and 31.8 mg (46.8%) of epoxide (VII) as a light yellow oil with the following characteristics: [α]$_D^{18}$ 31.2° (c 0.64, MeOH); IR (film) 2975, 2925, 2875, 1670, 1630, 1470, 1420, 1255, 1240, 1130, 915, 105, 880, 820, 800 cm$^{-1}$; $^1$H NMR δ6.57 (1H, dd, J=9.0, 2.0 H$_Z$), 6.37 (1H, dd, J=2.0, 0.4 H$_Z$), 5.92 (1H, d, J=9.0 H$_Z$), 3.62 (1H, m), 2.83 (1H, dd, J=6.8, 4.3 H$_Z$), 2.26 (1H, dd, J=6.8, 2.0 H$_Z$), 1.25 (3H, s), 1.18 (3H, s).

ANTIVIRAL AND ANTITUMOR ACTIVITIES OF THE COMPOUNDS OF THE INVENTION

The following assay method was utilized to illustrate the antiviral effectiveness of the compound of Formula II.

Day 1:
(1) Remove 75 cm$^2$ culture flasks from incubator (these were plated the previous week).
(2) Aspirate medium.
(3) Wash with 10 ml PBSA or Puck's Saline.
(4) Aspirate.
(5) Wash a second time with 10 ml PBSA or Puck's Saline.
(6) Aspirate.
(7) Add 2 ml trypsin/EDTA. Incubate until cells detach (10-20 min).
(8) Once detached, shake vigorously and immediately add 8 ml medium and shake again.
(9) Count cells. (To 0.5 ml cell suspension add 0.1 ml trypan blue. Wait 5-10 minutes. Count 4 corner squares and middle square of 5×5 array in hemocytometer. Blue cells are dead. Total count per 10 ml in culture flask=# live cells×6×10$^5$).
(10) Maintain cell line by adding 3×10$^6$ cells to another 75 cm$^2$ culture flask. Bring to 30 ml with fresh medium.
(11) For assay, add 1×10$^6$ cells to each well (6 wells per culture dish). Bring each well to 2 ml with fresh medium.
(12) Incubate overnight at 37° C.

Day 2:
(1) Aspirate medium.
(2) Add 0.5 of medium containing 200 pfu HSV-I.
(3) Incubate 10$^2$ hr with a small amount of shaking.
(4) Add 2 ml MC-4000 to each well.
(5) Place disks on surface and push through (1 mg/disc, 0.5 mg/disc, 0.25 mg/disc, etc. for crude extracts).
(6) Incubate 48 hr. (making sure dishes remain level).

Day 4:
(1) Add 2 ml neutral red medium.
(2) Incubate overnight.

Day 5:
(1) Read wells, e.g. compound of Formula II 16 (++) where 16 indicates zone of cytotoxicity as the diameter in mm (6 mm to 16 mm) and (++) indicates the inhibition of plaque formation: complete inhibition (+++), a few plaques around the outside of well (++), definite inhibition (+), questionable inhibition (+/−), no inhibition (−), and no conclusion due to complete cytotoxicity.

Day 7:
Begin cycle again at Day 1.

II RECIPES

CULTURE MEDIUM
- 1 L GIBCO MEM (plus non-essential a.a.'s with Earle's Salts).
- 2.2 g NaHCO$_3$
- 50 ml calf serum
- 105 units penicillin
- 50 mg streptomycin

MC-4000
- 500 ml CULTURE MEDIUM made to half volume (twice as concentrated)
- 500 ml v/w 4000 cps methyl cellulose

NEUTRAL RED MEDIUM (always make fresh)
- 500 ml CULTURE MEDIUM made to half volume (twice as concentrated)
- 500 ml 4% v/w 15 cps methyl cellulose
- 100 mg neutral red from stock solution

PUCK'S G SALINE SOLUTION
to 1 L distilled H$_2$O add:
- 8.00 g NaCl
- 0.40 g KCl
- 0.15 g KH$_2$PO$_4$
- 0.29 g Na$_2$HPO$_4$.7H$_2$O
- 2.0 ml 1% phenol red
- 1.10 g glucose
- autoclave

TRYPSIN-EDTA
for 1 L:
- "dissolve" 2 g DIFCO 1-250 trypsin plus 0.2 g EDTA in 100 ml PUCK'S SALINE.
- Sterile filter.
- Add to 900 ml sterile PUCK'S SALINE.

PBSA
to 1 L distilled H$_2$O Add:
- 8.00 G NaCl
- 0.20 g KCl
- 1.50 g Na$_2$HPO$_4$.7H$_2$O
- 0.25 g KH$_2$PO$_4$
- autoclave.

The results at Day 5 for the compound of Formula II indicates definite antiviral activity 16(++) for the compound. The compound of Formula II shows antiviral activity in minimal effective amounts of from 50 to 100 micrograms for 25 to 80 plaque forming units of virus cells.

The following assay method was utilized to illustrate the antitumor effectiveness of the compounds of formulas II, IV, V, VI and VII.

L1210 And P388 MOUSE LEUKEMIA CELL CYTOXICITY ASSAY 24-WELL PLATE SCREENING ASSAY AND TUBE ASSAY PROTOCOL

MATERIALS UTILIZED

Media—Dulbeccos with glucose and pyruvate (Biologos, Inc) with 10% horse serum, (Biologos, Inc) and 1.0 µg/ml gentamicin (Gibco). Cells—L1210 and P-388 mouse leukemia cells (American Type Culture Collection) in media at a concentration of 5×10$^4$ cells/ml. Sterile 24-well culture plates (Nunc) for screening or 12×75 mm glass culture tubes (Becton-Dickinson) for tube assay. Microdispenser with 1 to 5 µl increments (Drummond Scientific Co. Broomall Pa). Finnpipette with 5 to 50 µg increments and Finnpipette with 50 to 200 µl increments.

PROCEDURE

1. A sample of the composition to be assayed is added to each well or tube in an amount of from 200 µg/ml and 100 µg/ml for screening. For DDC of known active compounds use log concentrations from 100 µg/ml to 0.01 µg/ml for range-finding assay; when range has been determined, use five concentrations between highest and lowest active concentrations.

2. Add 2.0 ml of 5×10$^4$ cell suspension in media to each well or tube. Tubes are loosely covered with parafilm.

3. Incubate in 5% CO$_2$ incubator 48 hours.

4. Visually read plates with inverted microscope, comparing with solvent control. Assign activity as follows:
- 0 = 90–100% of control growth
- 1+ = 75–89% of control growth
- 2+ = 50–74% of control growth
- 3+ = 25–49% of control growth
- 4+ = 25% of control growth.

Repeat all positive samples using tube assay.

5. For Tube assays—Mix tube well on vortex and remove 0.5 ml aliquot and add to 9.5 ml nf diluent fluid (Isoton - Coulter) in Accuvette (Coulter) and mix well by inversion immediately before counting, taking care not to produce excessive bubbles. Count on Coulter Counter (Counter is set to count 0.5 ml of the solution; therefore counts may be converted to cell/ml in original assay tube by multiplying count by 40.

Positive control—Vinblastine or Vincristine in aqueous solution.

Final Conc of Vinblastine or Vincristine control (use 2 µl/assay)

| Solution Cnnc. | Amt added | Final Conc. in test |
| --- | --- | --- |
| 10 mg/ml | 2 µl | 10 µg/ml |
| 1 mg/ml | 2 µl | 1 µg/ml |
| 0.1 mg/ml | 2 µl | 0.1 µg/ml |
| 0.01 mg/ml | 2 µl | 0.001 µg/ml |

Notes: For solvents other than water, allow solvent to evaporate from tube or well in hood. Chloroform and butanol cannot be used in the plastic 24-well plates—use glass tubes. Always run a solvent control in duplicate in the last two wells of each plate or four tubes for each rack of 72 or less tubes. Also run four wells or tubes with media and cells only per run of plates or tubes. When using volumes of aqueous solutions greater than 200 µl, dry sample and bring up to desired concentration in media.

The results of the above assay show compounds of formulae II, V, VI and VII are cytotoxic in vitro against P-388 murine leukemia cells showing estimated ID$_{50}$'s (dose which kills 50% of the cells) of 37, 70, 70 and 5 micrograms per milliliter respectively. Compounds IV, V, VI and VII are cytotoxic in vitro against L-1210 murine leukemia cells showing 15%, 17%, 41% and 25% survival at 200 micrograms per milliliter respectively. Compound VII shows an estimated ID$_{50}$ of 0.7 micrograms per milliliter against L-1210 murine leukemia cells. The following table summarizes these results.

TABLE

| Composition of Formula | P-388 (ID50) | L-1210 |
| --- | --- | --- |
| II | 37 µg/ml | 100% survival at 200 µg/ml |
| IV | not tested | 15% survival at 200 µg/ml |
| V | 70 µg/ml | 17% survival at 200 µg/ml |

TABLE-continued

| Composition of Formula | P-388 (ID50) | L-1210 |
|---|---|---|
| VI | 70 μg/ml | 41% survival at 200 μg/ml |
| VII | 5 μg/ml | 28% survival at 200 μg/ml (ID50 0.7 μg/ml) |

The scope of the present invention is not limited by the description, examples, and suggested uses herein and modifications can be made without departing from the spirit of the invention. For example, it may be noted that other derivatives of the cyclohexadienones of example 1 such as a fluorinated cyclohexadienone may possess antiviral or antitumor activity analogous to those preferred embodiments described above. Further, the compositions described herein may have other useful applications such as, for example, analgesic applications. Thus, it is intended that the present invention cover the modifications and variations of this invention provided that they come within the scope of the appended claims and their equivalents.

What is claimed is:

1. A composition of the general formula:

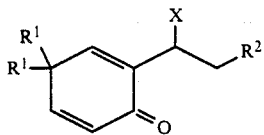

wherein both $R^1$ groups are the same or different and are hydrogen or a lower alkyl group, X is a lower alkyl, hydroxy, lower alkoxy, lower acyloxy, fluoro, chloro, bromo or iodo group, and $R^2$ is hydroxy, a lower acyloxy group or halogen.

2. A composition according to claim 1 wherein $R^1$ is a methyl group.

3. A composition according to claim 1 wherein $R^2$ is an acyloxy group of formula

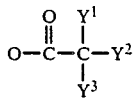

wherein $Y^1$, $Y^2$, and $Y^3$ are the same or different and are selected from the group consisting of a lower alkyl group, or hydrogen.

4. A composition according to claim 1 wherein X is methyl, methoxy, chloro or bromo.

5. A composition of the formula:

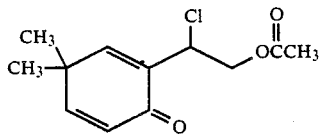

6. An antiviral composition comprising, as active ingredient, an effective antiviral amount of one or more of the compositions of claim 1 and a non-toxic pharmaceutically acceptable carrier or diluent.

7. An antiviral composition comprising, as active ingredient, an effective antiviral amount of one or more of the compositions of claim 3 and a non-toxic pharmaceutically acceptable carrier or diluent.

8. An antiviral composition comprising, as active ingredient, an effective antiviral amount of the composition of claim 5 and a non-toxic pharmaceutically acceptable carrier or diluent.

9. A method for inhibiting viruses in a host comprising contacting a virus with an effective antiviral amount of one or more compositions of claim 1.

10. A method for inhibiting viruses in a host comprising contacting a virus with an effective antiviral amount of one or more compositions of claim 3.

11. A method for inhibiting viruses comprising contacting a virus with an effective antiviral amount of the composition of claim 5.

12. An antitumor composition comprising, as active ingredient, an effective antitumor amount of one or more of the compositions of claim 1 and a non-toxic pharmaceutically acceptable carrier or diluent.

13. A method for inhibiting tumors in a host comprising contacting a tumor with an effective antitumor amount of one or more compositions of claim 1.

14. An antitumor composition effective against human lung, colon or mammary tumors comprising an effective antitumor amount of one or more compositions according to claim 1 and a non-toxic or pharmaceutically acceptable carrier or diluent.

15. An antitumor composition effective against animal lung, colon or mammary tumors comprising an effective antitumor amount of one or more compositions according to claim 1 and a non-toxic pharmaceutically acceptable carrier or diluent.

16. The method according to claim 13 wherein the tumors inhibited are selected from the group consisting of human lung, colon or mammary tumors.

17. The method according to claim 13 wherein the tumors inhibited are animal tumors.

18. A process to produce a composition according to the general formula of claim 3

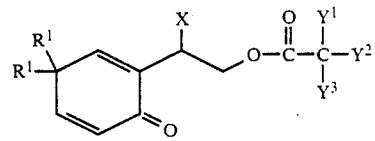

comprising the steps of:
collecting red algae;
contacting said algae with a first organic solvent selected from the group consisting of acetone, methyl ethyl ketone, ethyl acetate and methyl isobutyl ketone to obtain a first extract comprising a hydroxy composition according to formula A:

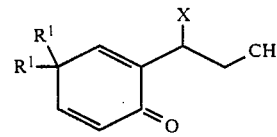

wherein $R^1$ and X have the same meaning as recited in claim 3 and $Y^1$, $Y^2$ and $Y^3$ are hydrogen;
admixing said first extract with a second organic solvent selected from the group consisting of methylene chloride, chloroform, trichloroethylene and a lower alkane to produce a second extract;
removing the second solvent extract containing a hydroxy composition according to formula A;

isolating said hydroxy composition of formula A by chromatography;

acetylating said hydroxy composition of formula A; and isolating a composition according to claim 3.

19. The process according to claim 18 wherein the red alga is *Desmia hornemanni*.

20. The process according to claim 18 wherein the first solvent is acetone and the second solvent is methylene chloride; the alcohol derivative is isolated by chromatography on a silica gel column by eluting with a mixture of hexane and acetone; a major fraction from the silica gel column chromatography is further separated on a thin layer chromatography grade silicon dioxide column utilizing flash chromatography to obtain said alcohol derivative and acetylating said alcohol derivative by treatment with a mixture of acetic anhydride and pyridine.

* * * * *

UNITED STATES PATENT AND TRADEMARK OFFICE
CERTIFICATE OF CORRECTION

PATENT NO. : 4,921,873

DATED : May 1, 1990

INVENTOR(S) : Tatsuo Higa, Kenneth M. Snader

It is certified that error appears in the above-identified patent and that said Letters Patent is hereby corrected as shown below:

Column 2: line 58: "$R_1$" should read --$R^1$--; line 61: "$R_2$" should read --$R^2$--;

Column 10: line 26: "$CH_2CH_2$" should read --$CH_2Cl_2$--.
Column 13: line 65: "50 $\mu g$" should read --50 $\mu l$--.
Column 14: line 35: "Cnnc." should read --Conc.--.
Claim 18: Structure A: "CH" should read --OH--.

Signed and Sealed this

Seventeenth Day of September, 1991

Attest:

HARRY F. MANBECK, JR.

*Attesting Officer*   *Commissioner of Patents and Trademarks*